(12) United States Patent  (10) Patent No.: US 8,007,443 B2
Newman  (45) Date of Patent: Aug. 30, 2011

(54) ASYMMETRIC INDUCTIVE BAND

(75) Inventor: Richard Newman, Templestone (AU)

(73) Assignee: Compumedics Limited, Victoria (AU)

( * ) Notice: Subject to any disclaimer, the term of this patent is extended or adjusted under 35 U.S.C. 154(b) by 1512 days.

(21) Appl. No.: 10/740,472

(22) Filed: Dec. 22, 2003

(65) Prior Publication Data

US 2004/0225227 A1    Nov. 11, 2004

Related U.S. Application Data

(63) Continuation of application No. PCT/IB02/03362, filed on Jun. 20, 2002.

(60) Provisional application No. 60/300,162, filed on Jun. 22, 2001.

(51) Int. Cl.
  *A61B 5/08*    (2006.01)
(52) U.S. Cl. .................. 600/534; 600/529; 600/538
(58) Field of Classification Search .................. 600/534
  See application file for complete search history.

(56) References Cited

U.S. PATENT DOCUMENTS

| 4,817,625 A | | 4/1989 | Miles |
| 4,893,077 A | * | 1/1990 | Auchterlonie ........... 324/207.17 |
| 5,543,012 A | | 8/1996 | Watson et al. |
| 5,815,091 A | * | 9/1998 | Dames et al. ............ 340/870.34 |
| 5,913,830 A | | 6/1999 | Miles |
| 6,624,624 B1 | * | 9/2003 | Karrer et al. .............. 324/117 R |
| 2002/0038799 A1 | * | 4/2002 | Laken et al. .................. 219/476 |

* cited by examiner

*Primary Examiner* — Robert L Nasser
(74) *Attorney, Agent, or Firm* — Sughrue Mion, PLLC

(57) ABSTRACT

The present invention includes an asymmetric inductive band that preferably has a conductor affixed from a first edge of a conductor substrate and looped across said substrate. A first and a second section of the conductor preferably is formed having "hairpin-like" features at some or all intermediate endpoints, or pivot locations, at discrete points along the length thereof. In addition, the first and the second section are arranged in an asymmetric relation to each other and, in general, each, of the hairpin-like features do not preferably directly oppose another of said features. The hairpins are preferably connected by a sawtooth shaped conductor that also contributes to the change in self-inductance when stretched, in addition to the apex, or hairpin, shape of the conductor.

19 Claims, 3 Drawing Sheets

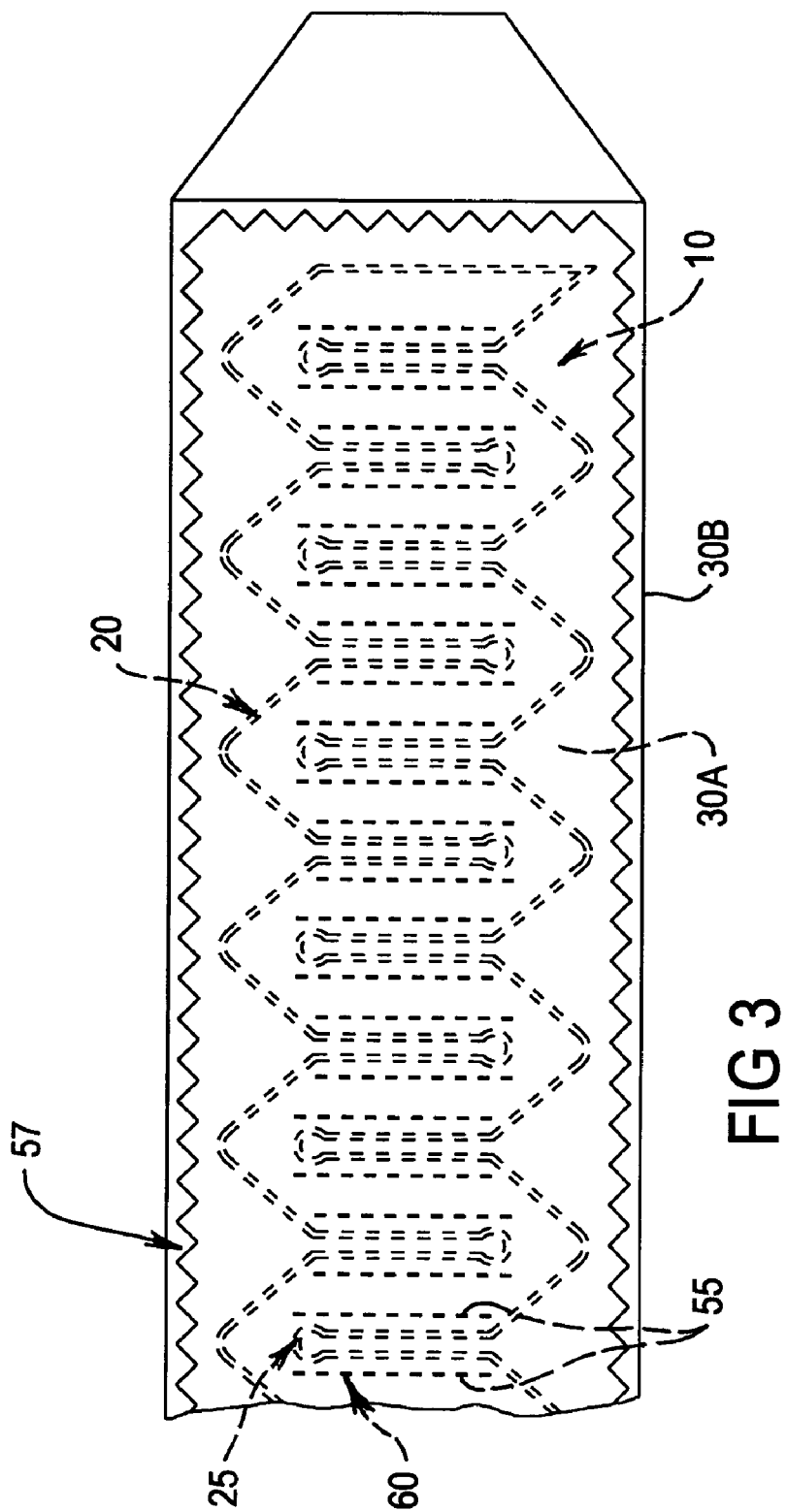

ASYMMETRIC INDUCTIVE BAND

This application is a Continuation of copending PCT International Application No. PCT/IB02/03362 filed on Jun. 20, 2002, which designated the United States, and on which priority is claimed under 35 U.S.C. § 120, the entire contents of which are hereby incorporated by reference, and which claims priority under 35 U.S.C. § 119(e) to U.S. Provisional application No. 60/300,162, filed Jun. 22, 2001.

FIELD OF THE INVENTION

The present invention relates to the field of respiration monitoring. In particular, the present invention is directed to an improved inductive band for indirectly measuring the expansion and contraction of the circumference of a subject, and determining the volume and rate of respiration of that subject.

BACKGROUND OF THE INVENTION

Many different types of inductive bands have been invented and used over the past several decades. Inductive vests and other transducers for converting breathing to quantifiable signals have also been developed. Some bands are designed to fully encircle a subject around the thorax and/or abdomen and others to partially encircle the subject.

For example, U.S. Pat. No. 4,817,625 teaches the use of enclosed, symmetrical top and bottom windings closely juxtaposed in an inductive band which has substantially enclosed areas throughout. U.S. Pat. No. 5,913,830 discloses the use of alternating active and inactive segments on an inductive band, wherein the active segments form substantially enclosed areas.

A need exists in the art for a more sensitive inductive transducer band that is readily adjustable and compact among other needs in the art for inductive transducer bands.

SUMMARY OF THE INVENTION

The present invention is directed to an asymmetric inductive band that preferably comprises a conductor affixed from a first edge of a conductor substrate and looped across said substrate. A first and a second section of the conductor preferably are formed having "hairpin-like" features at some and/or all intermediate endpoints, or pivots, at several locations along the length thereof. In addition, the first and the second sections are arranged in an asymmetric relation to each other and, in general, each of the hairpin-like features preferably do not directly oppose another of the hairpin-like features.

The following are advantages and/or engineering considerations resulting from the "hairpin" features, or any other features of the conductor or band. The main advantage over existing designs is that the hairpin feature is more sensitive, particularly when the band excursions from a non-distended position are small. When the band is not stretched, the adjacent conductors of the "hairpin" shape are almost touching, so even a slight extension of the band will increase the gap in the "hairpin", causing a relatively large change in self-inductance compared with existing shapes. The change in inductance is measured by an electronic circuit to which the inductive respiratory band is connected, as is known and used in the art.

The return winding (bottom half of the conductor) has the same pattern as the top but is shifted so that the hairpin features on the return winding do not directly oppose the hairpin features on the top winding. This configuration has the desirable properties of increasing the number of hairpins on the conductor which, in turn, increases the sensitivity of the conductor to even very small changes in the subject's circumference.

The hairpins are connected by a sawtooth shaped conductor that also contributes to the change in self-inductance when stretched, in addition to the apex, or hairpin, shape of the conductor. In practice, the sawtooth shape provides room for the hairpin from the opposing conductor winding. In fact, the preferred configuration of the conductor of the present invention exhibits an overlapping juxtaposition, or relation, between the apex, or hairpin, features along a central longitudinal axis of the elongate distensible band that supports both portions of the elongate conductor.

The asymmetric inductive band according to the present invention is fastened to a distensible backing material that preferably encircles only a portion of the chest or abdomen of a human subject. A strap (or straps) of non-distensible material is attached to the distensible material so as to encircle the subject. The band is connected to a preferably toroidal-shaped impedance matching transformer (which is also attached to the distensible material) and by two other conductors to an electronics circuit which converts inductance changes in the asymmetric inductive band to a voltage signal which is proportional to the change in length of the distensible band as a subject ventilates or inhales and exhales, and therefore is proportional to the change in circumference of the subject and thus the volume (and rate of) respiration of the subject. Such electronics circuits are known and used in the art.

BRIEF DESCRIPTION OF THE DRAWINGS

FIG. 3 is a top view of another embodiment of the present invention, showing an example of the stitching pattern used to make the inductive band.

DETAILED DESCRIPTION OF PREFERRED EMBODIMENTS OF THE PRESENT INVENTION

Figure 1:
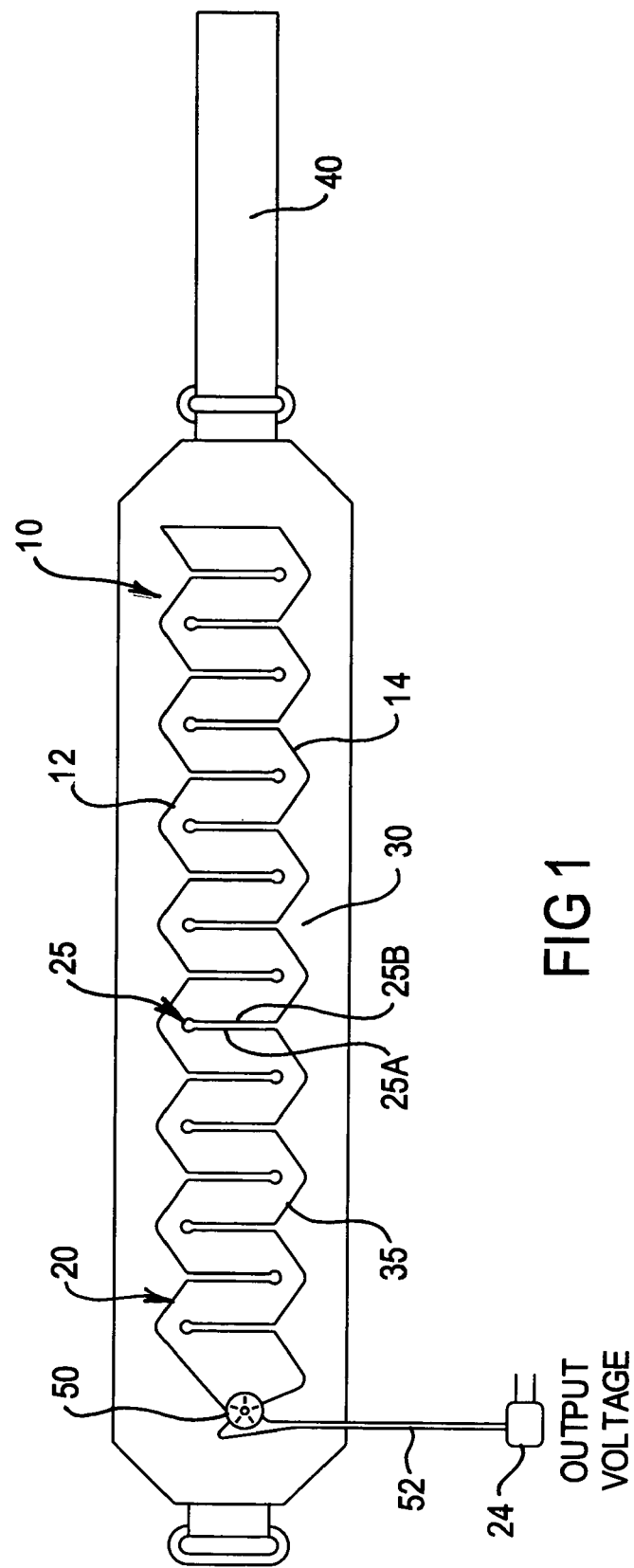
FIG. 1 is a plan view of a preferred embodiment of the present invention.

The present invention is directed to an asymmetric inductive band 10 as shown in FIG. 1 for use in measuring respiration of a subject. An asymmetric inductive band 10 according to the present invention preferably comprises an elongate conductor 20 having a first portion 12 and a second portion 14 disposed on a substrate of distensible material 30. Said distensible material is preferably mechanically coupled to a length of non-distensible material 40, or, more typically, a belt having a fastener, buckle, hook and loop patch material, a pair of interlocking snaps, a portion of friction fitting material, a knot, a button, a cleat, a length of stitching, an adhesive, a zipper and the like for coupling the distensible material 30 to the non-distensible material 40 to encircle a portion of the torso, thorax and/or abdomen of a subject during use.

The present invention may consist of simply the elongate conductor as taught herein with any backing material or substrate, transformer or other additional components either eliminated or disposed remotely from but in electrical communication with the elongate conductor. In this embodiment or form of the present invention, either a first portion or a second potion (or both portions) may fully encircle the subject or may encircle only a portion of the subject and may be coupled to remote electronic circuitry 24 via a wireless transceiver or other telemetry pair such as infrared, UV, or other frequency or frequencies of electromagnetic radiation.

In use, an optional liner or layers of liner materials may be added to protect the inductive band transducer and/or to render same more comfortable to the subject. The conductor 20 may be affixed to the distensible substrate 30 with adhesive, wire, stitching, or retained in pockets or otherwise constrained by features of the distensible substrate 30.

The conductor 20 may be fabricated from any electrically conducting metal, composite material, alloy, resin-based material, polymer or may be made of trace materials embedded into the distensible substrate 30 as long as the material conducts electricity sufficiently to produce signals susceptible of accurate measurement. Preferably, the conductor 20 is insulated using conventional wire insulation. In one preferred embodiment, when the conductor is in the non-distended state, legs 25A and 25B of each hairpin 25 are separated only by the insulation.

Advantages or engineering considerations resulting from a series of "hairpin" (or apex) features 25, or any other features of the conductor or band 20 include the following. The main advantage of such features 25 over existing designs is that they are more sensitive, particularly when the band excursions from a non-distended state are small, that is, when the distensible material 30 is stretched only slightly and the conductor 20 thus creates a signal, thereof. When the distensible band 30 is not stretched, the adjacent portions 12 and 14 of the conductor 20, and in particular, the hairpin features 25, are almost touching, so even a slight extension of the band 30 will increase the gap between each leg 25A and 25B of each hairpin feature 25, causing a relatively large change in self-inductance compared with existing and prior inductive bands.

Figure 2A:
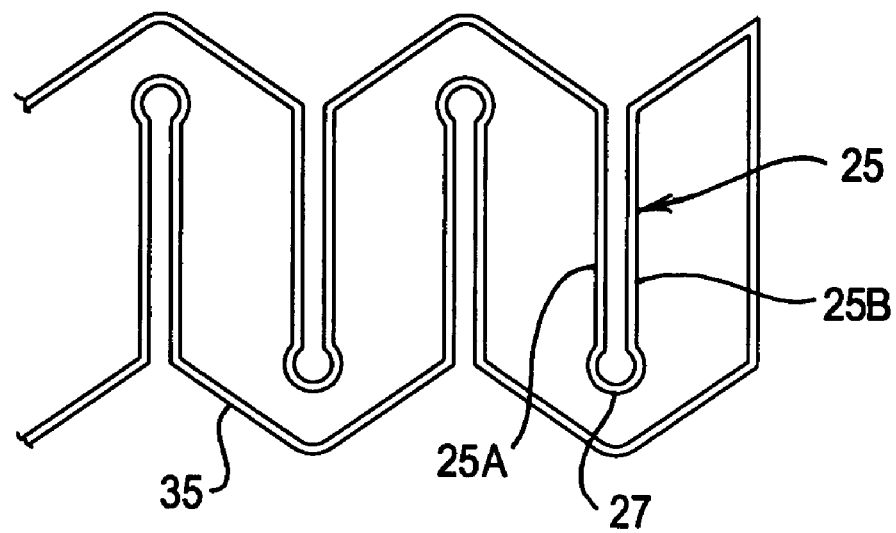
FIG. 2A is an enlarged view of a portion of the conductor embodiment depicted in FIG. 1, with the conductor in a non-distended state.
Figure 2B:
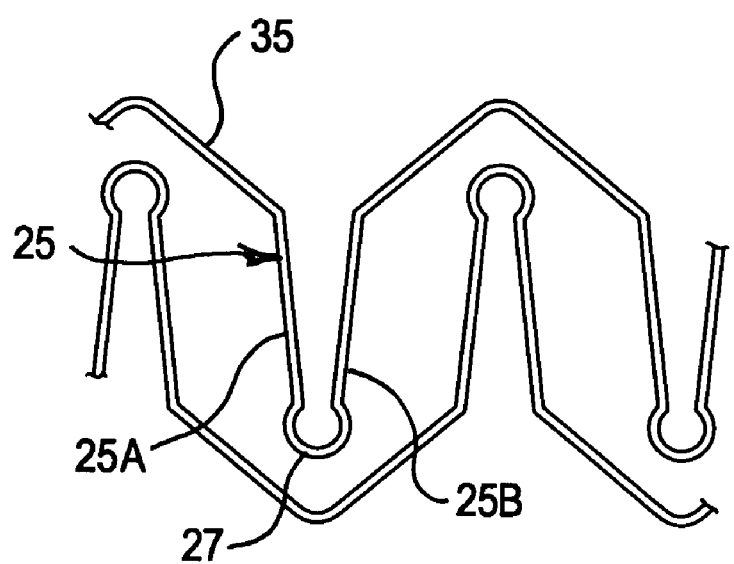
FIG. 2B is an enlarged view of a portion of the conductor embodiment depicted in FIG. 1, with the conductor in a distended state.

Referring to FIGS. 2A and 2B, each leg portion 25A or 25B of hairpin feature 25 may be oriented in a parallel or in a slightly divergent orientation relative to the other leg portion. The apex feature 27 of each hairpin feature 25 is preferably semi-circular, shaped as the letter "C" having a more or less common radius. When the conductor 20 is distended, the leg portions 25A and 25B of the hairpin features 25 assume more of the slightly divergent orientation. As is known and used in the art, the change in inductance resulting from the extension of the distensible material 30 that moves the conductor 20 is typically and preferably measured by a remote electronic circuit 24 to which inductive respiratory band 10 is connected. The remote electronic circuit 24 typically includes an oscillator to generate a band excitation or carrier signal and a frequency-to-voltage converter or AM demodulator to convert changes in inductance due to band distention from the original configuration into a voltage which can be recorded or measured.

The return winding 14 of the conductor 20 (i.e., the bottom portion of the conductor 20 as depicted in FIG. 1) preferably has the same pattern as the top portion 12, or outbound winding, but is shifted relative to the top portion 12 so that the hairpin features 25 do not clash or contact one another. This embodiment has the desirable properties of increasing the number of hairpin features 25 and therefore the sensitivity of the inductive band to even small changes in the subject's circumference. The hairpin features 25 of the present invention are connected by a sawtooth shaped intermediate sections 35 of the conductor 20, and these intermediate sections 35 also contribute to the change in self-inductance when stretched. In practice, the sawtooth shape provides room for the hairpin features 25 from the opposing portions 12 and 14 of the conductor winding 20.

The conductor 20 may be integrated into the distensible substrate 30 and may be affixed to or woven into a specific configuration as long as the conductor 20 is electrically insulated relative to other parts of the conductor 20 and, if necessary, from the substrate 30 (and/or the subject).

The conductor 20 is preferably fastened to a distensible backing material 30 that only encircles a portion of the chest or abdomen of a human subject. A strap (or straps) of non-distensible material 40 is attached to the distensible material 30 so as to encircle the subject. The conductor 20 is connected to a toroidal impedance matching transformer 50 (which is also attached to the distensible material 30) and by two conductors 52 to the remote electronics circuit 24 which is able to convert inductance changes in the conductor band 20 to a voltage which is proportional to the change in circumference of the subject, as is known and used in the art.

Another advantage of the asymmetric inductive band of the present invention is that it can be easily manufactured using conventional sewing machines, in contrast with conventional symmetric inductive bands which require special apparatus to manufacture such bands, as is described in U.S. Pat. No. 5,543,012. In the embodiment shown in FIG. 3, a top piece of distensible material 30A is placed over a bottom piece of distensible material 30B, and two vertical rows of stitching 55 are sewn into the material using a conventional sewing machine, to form a pocket 60 for each hairpin 25. The conductor 20 is bent into shape on a jig, and each hairpin 25 is placed into a pocket 60 to hold the hairpin 25 in position while the perimeter 57 of the band 10 is sewn. Because no stitching needs to cross the band itself, a conventional sewing machine can be used to make the inductive band of the present invention.

Additional advantages and modifications will readily occur to those skilled in the art. The invention in its broader aspects is, therefore, not limited to the specific details, representative apparatus and illustrative examples shown and described. Accordingly, departures from such details may be made without departing from the spirit or scope of the applicant's general inventive concept.

What is claimed is:

1. An asymmetric inductive band for monitoring respiration in a subject, the asymmetric inductive band comprising:
   an elongate conductor having a first portion and a second portion, said first portion and said second portion being arranged in an asymmetric relationship to each other;
   a processor receiving a signal from the elongate conductor and outputting a respiration signal;
   each of said first portion and said second portion having a series of hairpin features at a plurality of positions in a lengthwise direction thereof, said hairpin features being connected by sawtooth-shaped intermediate sections;
   said hairpin features each having a first straight leg portion, a second straight leg portion, and an apex portion connecting the first straight leg portion to the second straight leg portion, the first straight leg portion and the second straight leg portion being closely spaced from each other; and
   the hairpin features of the first portion and the hairpin features of the second portion being disposed in a spaced-apart relationship and overlapping each other along a common longitudinal axis disposed between the first portion and the second portion of the elongate conductor;
   wherein the asymmetric inductive band is distensible.

2. An inductive band according to claim 1 characterized in that it further includes a distensible conductor support substrate in supporting relation to the elongate conductor.

3. An inductive band according to claim 2 characterized in that the elongate conductor is woven or stitched into the distensible conductor support substrate.

4. An inductive band according to claim 2 characterized in that it further includes a non-distensible band, wherein the distensible conductor support substrate is coupled to the non-distensible band with at least one of: a pair of hook and loop patch material, a buckle, portion or friction fitting material, a knot, a button, a cleat, a length of stitching, an adhesive, a zipper and the like.

5. An inductive band according to claim 1 characterized in that the elongate conductor is fabricated from an electrically-conducting material selected from a group consisting of metal, composite material, alloy, resin-based material or polymer material.

6. An inductive band according to claim 1 characterized in that it further includes a transformer electrically coupled to each end of the elongate conductor.

7. An inductive band according to claim 1 characterized in that each hairpin feature includes a semi-circular apex portion.

8. An inductive band according to claim 1, wherein the elongate conductor is adapted to be placed on the epidermis of the subject.

9. An inductive band according to claim 1, wherein the first straight leg portion and second straight leg portion are capable of diverging from each other when the circumference of the subject increases.

10. An inductive band according to claim 9, wherein said diverging causes a change in an inductance of the conductor.

11. An electrical conductor trace pattern for an inductive band comprising:
    a first portion of conductive material; and
    a second portion of conductive material;
    wherein said first portion and said second portion are arranged in an asymmetric relationship to each other, and
    a processor receiving a signal from the elongate conductor and outputting a respiration signal;
    wherein each of said first portion and said second portion have a series of hairpin features at a plurality of positions in a lengthwise direction thereof, said hairpin features being connected by sawtooth-shaped intermediate sections;
    wherein said hairpin features each have a first straight leg portion, a second straight leg portion, and an apex portion connecting the first straight leg portion to the second straight leg portion, the first straight leg portion and the second straight leg portion being closely spaced form each other;
    wherein the hairpin features of the first portion and the hairpin features of the second portion are disposed in a spaced-apart relationship and overlap each other along a common longitudinal axis disposed between the first portion and the second portion of the conductive material; and
    wherein the inductive band is distensible.

12. A self-inductance sensor for measuring the change in circumference of an object, comprising:
    an elongate conductor having a series of spaced geometric shapes formed therein, the geometric shapes disposed on either side of a longitudinal axis of said elongate conductor,
    a processor receiving a signal from the elongate conductor and outputting a respiration signal;
    wherein at least two of said geometric shapes are hairpin-shaped;
    wherein each geometric shape has an apex extending from said longitudinal axis;
    wherein the apices of successive geometric shapes on a side of said longitudinal axis are offset from the apices of successive geometric shapes on the opposite side of said longitudinal axis; and
    wherein the self-inductance sensor is distensible.

13. A self-inductance sensor according to claim 12 characterized in that it further includes a distensible conductor support substrate in supporting relation to the elongate conductor.

14. A self-inductance sensor according to claim 13 characterized in that the elongate conductor is woven or stitched into the distensible conductor support substrate.

15. A self-inductance sensor according to claim 12 characterized in that it further includes a non-distensible band, wherein the distensible conductor support substrate is coupled to the non-distensible band with at least one of: a pair of hook and loop patch material, a buckle, portion or friction fitting material, a knot, a button, a cleat, a length of stitching, an adhesive, a zipper and the like.

16. A self-inductance sensor according to claim 12 characterized in that the elongate conductor is fabricated from an electrically-conducting material selected from a group consisting of metal, composite material, alloy, resin-based material or polymer material.

17. A self-inductance sensor according to claim 12 characterized in that it further includes a transformer electrically coupled to each end of the elongate conductor.

18. A self-inductance sensor according to claim 12 characterized in that each apex is a semi-circular shape.

19. A self-inductance sensor according to claim 12, wherein the elongate conductor is adapted to be placed on the epidermis of the object.

* * * * *